US006908910B2

United States Patent
D'Amato et al.

(10) Patent No.: US 6,908,910 B2
(45) Date of Patent: *Jun. 21, 2005

(54) ESTROGENIC COMPOUNDS AS ANTI-MITOTIC AGENTS

(75) Inventors: Robert John D'Amato, Lancaster, PA (US); Moses Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/077,142

(22) Filed: Feb. 15, 2002

(65) Prior Publication Data

US 2002/0165212 A1 Nov. 7, 2002

Related U.S. Application Data

(63) Continuation of application No. 09/243,158, filed on Feb. 2, 1999, now Pat. No. 6,528,676, which is a division of application No. 08/838,699, filed on Apr. 25, 1997, now Pat. No. 5,892,069, which is a division of application No. 08/571,265, filed on Dec. 12, 1995, now Pat. No. 5,661,143, which is a continuation of application No. 08/102,767, filed on Aug. 6, 1993, now Pat. No. 5,504,074, application No. 10/077,142, which is a continuation of application No. 09/436,610, filed on Nov. 9, 1999, now abandoned, which is a continuation of application No. 09/243,158.

(51) Int. Cl.[7] .............................................. A61K 31/56
(52) U.S. Cl. ....................................... 514/182; 514/912
(58) Field of Search ......................................... 514/182

(56) References Cited

U.S. PATENT DOCUMENTS

| 3,166,577 | A | | 1/1965 | Ringold et al. |
| 3,562,260 | A | | 2/1971 | De Ruggieri et al. |
| 4,552,758 | A | | 11/1985 | Murphy et al. |
| 4,634,705 | A | | 1/1987 | DeBernardis et al. |
| 4,808,402 | A | | 2/1989 | Leibovich et al. |
| 5,015,629 | A | * | 5/1991 | diZerega ...................... 514/16 |
| 5,504,074 | A | * | 4/1996 | D'Amato et al. ........... 514/182 |
| 5,661,143 | A | * | 8/1997 | D'Amato et al. ........... 514/182 |
| 6,528,676 | B1 | | 3/2003 | D'Amato et al. |
| 2002/0058612 | A1 | * | 5/2002 | Franco |
| 2003/0175961 | A1 | * | 9/2003 | Herron |

FOREIGN PATENT DOCUMENTS

| EP | 0166937 A2 | 8/1986 |
| GB | 857080 | 12/1960 |
| GB | 857081 | 12/1960 |
| GB | 1570597 | 7/1980 |
| JP | 39005480 B | 4/1964 |
| JP | 41 000100 A | 1/1966 |
| JP | 42-928 B | 1/1967 |
| JP | 58-131978 | 8/1983 |
| JP | 63-119500 | 5/1988 |
| SU | 1240038 A1 | 10/1996 |
| WO | WO 87/02367 A3 | 4/1987 |
| WO | WO 88/08002 A1 | 10/1988 |
| WO | WO 93/19746 A1 | 10/1993 |

OTHER PUBLICATIONS

Simons, General concepts of angiogenesis.*
Benedict et al., Annals of Internal Medicine, vol. 136(a), pp. 54–71, 2002.*
Seegers et al., "The cytotoxic effects of estradio–17.beta. catecholestradiols and methoxyestradiols on dividing MCF–7 and HeLa cells." J. Steroid Biochem., vol. 32(6), pp. 797–809, 1989.*

(Continued)

Primary Examiner—Barbara P. Badio
(74) Attorney, Agent, or Firm—Kilpatrick Stockton LLP (57) ABSTRACT

The application discloses methods of treating mammalian diseases characterized by abnormal cell mitosis by administering estradiol derivatives including those comprising colchicine or combretastatin A-4 structural motifs of the general formulae found below in a dosage sufficient to inhibit cell mitosis. The application discloses novel compounds used in the methods.

5 Claims, 3 Drawing Sheets

OTHER PUBLICATIONS

*Research Plus Catalog*, pp.: 50–58, 1993.
Registry No.: 56933–77–8, *Chemical Abstracts*.
Registry No.: 56933–78–9, *Chemical Abstracts*.
Registry No.: 57380–15–1, *Chemical Abstracts*.
Registry No.: 71782–94–0, *Chemical Abstracts*.
Registry No.: 71782–95–1, *Chemical Abstracts*.
Registry No.: 101277–11–6, *Chemical Abstracts*.
Registry No.: 101429–40–7, *Chemical Abstracts*.
Registry No.: 162853–20–5, *Chemical Abstracts*.
Aboulwafa et al., Synthesis and evaluation for uterotrophic and antiimplantation activities of 2–substituted estradiol derivatives, *Steroids*, vol.: 57, pp.: 199–204, Apr. 1992.
Algire, G.H. et al., Vascular reactions of normal and malignant tumors in vivo. I. Vascular reactions of mice to wounds and to normal and neoplastic transplants, *Journal of the National Cancer Institute*, vol.: 6, pp.: 73–85, Aug. 1945.
Aliev et al., 54929q Synthesis of cycloalkyl derivatives of dihydric phenols and their ethers, *Chemical Abstracts*, vol.: 72, pp.: 370, 1970.
Barnes et al., Tumor Necrosis Factor Production in Patients with Leprosy, *Infection and Immunity*, vol.: 60 (4), pp.: 1441–1446, Apr. 1992.
Bindra et al., Studies in Antifertility Agents.8.Seco Steroids. 2. 5,6–Secoestradiol and Some Related Compounds, *Journal of Medicinal Chemistry*, vol.: 18 (9), pp.: 921–925, 1975.
Blickenstaff et al., Synthesis of Some Analogs of Estradiol, *Steriods*, vol.: 46 (4,5), pp.: 889–902, Oct. 1985.
Boyce et al., Some Preliminary Synthetical Studies with 5,6,7,8–Tetra–hydro–8–methylindane–1,5–dione, *Unknown*, pp.: 4547–4553, 1960.
Brandi et al., Bone endothelial cells as estrogen targets (Abstract only), *Calcif. Tissue Int.*, vol.: 53 (5), pp.: 312–317, 1993.
Brem, H. et al., Interstitial chemotherapy with drug polymer implants for the treatment of recurrent gliomas, *Journal of Neurosurgery*, vol.: 74, pp.: 441–446, Mar. 1, 1991.
Cambie et al., Aromatic Steroids. Part I. Oxidation Products of 3–Methoxyestra–1,3,5(10)–triene– 17βyl Acetate, *J. Chem. Soc.*, pp.: 2603–2608, 1968.
Corey et al., Applications of N,N–Dimethylhydrazones to Synthesis. Use in Efficient, Positionally and Stereochemically Selective C–C Bond Formation; Oxidative Hydrolysis to Carbonyl Compounds, *Tetrahedron Letters*, pp.: 3–6, 1976.
Corey et al., Facile Conversion of N,N–Dimethylhydrazones to Cabonyl Compounds by Cupric Ion–Catalyzed Hydrolysis, *Tetrahedron Letters*, vol.: 41, pp.: 36678–3668, 1976.
Crabbe, P., Cotton effect of the styrene chromophore (Abstract only), *Chem. Ind.*, vol.: 27, pp.: 917–918, 1969.
Durani et al., Seco–Oestradiols and Some Non–Steroidal Oestsrogens: Structural Correlates of Oestrogenic Action, *Journal of Steroid Biochemistry*, vol.: 11, pp.: 67–77, 1979.
Eder et al., Synthese von Ostradiol (in German—No translation available), *Chem. Ber.*, vol.: 109, pp.: 2948–2953, 1976.
Emons et al., Modulation der hypophysaren Sekretion von Luteinisierendem Hormon (LH) durch Ostrogene, *Focus MHL*, English Summary Only, vol.: 3, pp.: 221–228, 1986.
Fanchenko et al., Characteristics of the guinea pig uterus estrogen receptor system (Abstract only), *Byull. Eksp. Biol. Med.*, vol.: 85 (4), pp.: 467–470, 1978.

Fevig et al., A Short, Stereoselective Route to 16α(Substituted–alkyl)estradiol Derivatives, *Journal of Organic Chemistry*, vol.: 52, pp.: 247–251, 1987.
Field et al., Effect of Thalidomide on the Graft versus Host Reaction, *Nature*, vol.: 211 (5055), pp.: 1308–1310, Sep. 17, 1966.
Fieser et al., N–Methylformanilide, *Organic Synthesis Collective vol. 3*, vol.: 3, pp.: 590–591, 1955.
Flohe et al., Studies on the Hypothetical Relationship of Thalidomide–induced Embryopathy and Collagen Biosynthesis, *Arzncimitte/Forschung (Germany West)*, vol.: 31 (2), pp.: 315–320, Jan. 1, 1981.
Folkman et al., Angiogenesis Inhibition and Tumor Regression Caused by Heparin or a Heparin Fragment in the Presence of Cortisone, *Science*, vol.: 221, pp.: 719–725, Aug. 19, 1983.
Folkman, J., Tumor Angiogenesis: Therapeutic Implications, *New England Journal of Medicine*, vol.: 285 (21), pp.: 1182–1186, Nov. 18, 1971.
Folkman, J. et al., Induction of Angiogenesis During the Transition from Hyperplasia to Neoplasia, *Nature*, vol.: 339, pp.: 58–61, May 4, 1989.
Folkman, J. et al., Tumor Behavior in Isolated Perfused Organs in vitro Growth and Metastases of Biopsy Material in Rabbit Thyroid and Canine Intestinal Segment, *Annals of Surgery*, vol.: 164(3), pp.: 491–502, Sep. 1, 1966.
Gandhi et al., Mannich reaction of estrone, *Journal of Indian Chem. Soc.*, vol.: 39, pp.: 306–308, 1962.
Gaslini et al., Reaction of Eugenol with Synthesis Gas. Synthesis of 5,6,7,8–Tetrahydro–3–methoxy–2–napthol, *Journal of Organic Chemistry*, vol.: 29 (5), pp.: 1177–1180, May 1964.
Gimbrone, M.A. et al., Tumor Growth and Neovascularization: An Experimental Model Using the Rabbit Cornen, *Journal of the National Cancer Institute*, vol.: 52(2), pp.: 413–427, Feb. 1974.
Gimbrone, M.A. et al., Tumor dormancy in vivo by Prevention of Neovascularization, *Journal of Experimental Medicine*, vol.: 136, pp.: 261–276, 1972.
Gonzalez et al., Synthesis and Pharmacological Evaluation of 8αEstradiol Derivatives, *Steroids*, vol.: 40 (2), pp.: 171–187, Sep. 1982.
Gross, J.L. et al., Modulation of Solid Tumor Growth in vivo by bFGF (Abstract only), *Proceedings of the American Association of Cancer Research*, vol.: 31, pp.: 79, Mar. 1990.
Gunzler, V., Thalidomide–A Therapy for the Immunological Consequences of HIV Infection?, *Medical Hypothesis*, vol.: 30 (2), pp.: 105–109, Oct. 1989.
Gupta et al., Antifertility Agents. XIV. Secosteroids. VII. Synthesis of 2αand 2β, 6β–dimethyl– 3β–(p–hyroxyphenyl)–trans–bicyclo[4.3.0]nonan–7–ones and some related compounds (Abstract only), *Indian Journal of Chemistry*, vol.: 13 (7), pp.: 759–760, 1975.
Gupta et al., Studies in Antifertility Agents. Part XVIII. 2q6β–Diethyl–3β–(p–hydroxyphenyl)–trans–bicyclo[4.3.0]nonan–7β–ol and 6β–methyl–3β–(p–hydroxyphenyl)–2α–propyl– trans–bicyclo[4.3.0]nonan–7βol (Abstract only), *Indian Journal of Chemistry*, vol.: 19B (10), pp.: 886–890, 1980.
Gutierrez–Rodriguez et al., Treatment of Refractory Rheumatoid Arthritis—The Thalidomide Experience, *The Journal of Rheumatology*, vol.: 16 (2), pp.: 158–163, Feb. 1989.

Gutierrez–Rodriguez, O., Thalidomide—A Promising New Treatment for Rheumatoid Arthritis, *Arthritis and Rheumatism*, vol.: 27 (10), pp.: 1118–1121, Oct. 1984.

Hahnel et al., The Specificity of the Estrogen Receptor of Human Uterus, *Journal of Steroid Biochemistry*, vol.: 4, pp.: 21–31, 1973.

Handley et al., Chronic bullous disease of childhood and ulcerative colitis, *British Journal of Dermatology*, vol.: 127 (40), pp.: 67–68, Jul. 1, 1992.

Heney et al., Thalidomide treatment for chronic graft–versus–host disease, *British Journal of Haematology*, vol.: 78 (1), pp.: 23–27, May 1991.

Holker et al., The Reactions of Estrogens with Benzeneseleninic Anhydride and Hexamethyldisilazane, *J. Chem. Soc. Perkin Trans.*, vol.: 1, pp.: 1915–1918, 1982.

Hori, A. et al., Suppression of Solid Tumor Growth by Immunoneutralizing Monoclonal Antibody Against Human Basic Fibroblasts Growth Factor, *Cancer Research*, vol.: 51, pp.: 6180–6184, Nov. 15, 1991.

Imamura et al., Method for Manufacture of Dihydric Phenols (Abstract only), *USPATFULL 76:20259 US 3,950,437*, Apr. 13, 1976.

Ingber, D. et al., Synthetic analogues of fumagillin that inhibit angiogenesis and suppress tumor growth, *Nature*, vol.: 348, pp.: 555–557, Dec. 6, 1990.

Iriarte et al., Steroids (XCIV). Synthesis of 2–methyl and 1,2–dimethyl estrogens (Abstract only), *Tetrahedron*, vol.: 3, pp.: 28–36, 1958.

Jhingran et al., Studies in Antifertility Agents—Part XLI: Secosteroids–x: Syntheses of Various Stereoisomers of (+–)–2, 6β–diethyl–7α–ethynyl–3–(p–hydroxyphenyl)–trans–bicyclo[4.3.0]nonan–7β–ol., *Steroids*, vol.: 42 (6), pp.: 627–634, 1983.

Karwat, Separation and Recovery of Hydrogen Sulfide from Hydrocarbon Mixture, *Caplus DE 1103310*, Sep. 2, 1959.

Kim, K.J. et al., Inhibition of Vascular Endothelial Growth Factor–Induced Angiogenesis Suppresses Tumor Growth In Vivo, *Nature*, vol.: 362, pp.: 841–844, Apr. 29, 1993.

Knighton, D. et al., Avascular and Vascular Phases of Tumour Growth in the Chick Embyo, *British Journal of Cancer*, vol.: 35, pp.: 347–356, 1977.

Kole et al., Studies in Antifertility Agents. 11. Secosteroids.5.Sythesis of 9,11–Secostradiol, *Journal of Medicinal Chemistry*, vol.: 18 (7), pp.: 765–766, 1975.

Kovacs et al., Steroids. XXIII. Synthesis of 2– and 4–hydroxy and 2,4–dihydroxy derivatives of estrone and estradiol (Abstract only), *Acta Phys.Chem.*, vol.: 19 (3), pp.: 287–290, 1973.

Lewis, Richard J., *Hawley's Condensed Chemical Dictionary*, pp.: 577, Jan. 1993.

Lewis, Richard J., *Hawley's Condensed Chemical Dictionary*, pp.: 128–129, Jan. 1993.

Lien, W. et al., The blood supply of experimental liver metastases. II. A Microcirculatory study of the normal and tumor vessels of the liver with the use of perfused silicone rubber, *Surgery*, vol.: 68 (2), pp.: 334–340, Aug. 1970.

Liu et al., Total Synthesis of (+–)–$\Delta^{9(12)}$–Capnellene, *Tetrahedron Letters*, vol.: 26 (40), pp.: 4847–4850, 1985.

Loozen et al., An approach to the synthesis of 7.beta–amino estrogens (Abstract only), *Recl.: J.R. Neth.Chem. Soc.*, vol.: 102 (10), pp.: 433–437, 1983.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol.: 92, pp.: 11–32, 1986.

Michel et al., Inhibition of synaptosomal high–affinity uptake of dopamine and serotonin by estrogen agonists and antagonists (Abstract only), *Biochem. Pharmacol.*, vol.: 36 (19), pp.: 3175–3180, 1987.

Morisaki et al., Steroids. Lt. Aromatization reaction of the cross–conjugated dienone system by Zinc 9. (Abstract only), *Chem. Pharm. Bull.*, vol.: 14 (8), pp.: 866–872, 1966.

Naafs et al., Thalidomide Therapy An Open Trial, *International Journal of Dermatology*, vol.: 24 (2), pp.: 131–134, Mar. 1985.

Nambara et al., Microbial transformation products derived from steriods. 1. Synthesis of 1,2– and 3–dimethoxy–4–methylestratrienes (Abstract only), *Chem. Pharm. Bull.*, vol.: 20 (2), pp.: 336–342, 1972.

Nambara et al., Synthesis of 16β–Oxygenated Catechol Estrogen Methyl Ethers, New and Potential Metabolites, *Chemical & Pharmaceutical Bulletin*, vol.: 23 (7), pp.: 1613–1616, Jul. 1975.

Newkome et al., Synthesis of Simple Hydrazones of Carbonyl Compounds by an Exchange Reaction, *Journal of Organic Chemistry*, vol.: 31, pp.: 677–681, Mar. 1966.

Nguyen, M. et al., Elevated Levels of the Angiogenic Peptide Basic Fibroblast Growth Factor in Urine of Bladder Cancer Patients, *Journal of the National Cancer Institute*, vol.: 85 (3), pp.: 241–242, Feb. 3, 1993.

Numazawa et al., Novel and Regiospecific Synthesis of 2–Amino Estrogens via Zincke Nitration, *Steroids*, vol.: 41 (5), pp.: 675–682, 1983.

Pert et al., Preparations of 2,4–disubstituted estradiols (Abstract only), *Australian Journal of Chemistry*, vol.: 42 (3), pp.: 421–432, 1989.

Peters et al., 17–Desoxy Estrogen Analogues, *Journal of Medicinal Chemistry*, vol.: 32 (7), pp.: 1642–1652, 1989.

Pfeiffer et al., Are catechol estrogens obligatory mediators of estrogen action in the central nervous system? I. Characterization of pharmacological probes with different receptor binding affinities and catechol estrogen formation rates (Abstract only), *Journal of Endocrinology*, vol.: 110 (3), pp.: 489–497, 1986.

Powell et al., Investigation and Treatment of Orogenital Ulceration; studies on a Possible Mode of Action of Thalidomide, *British Journal of Dermatology*, vol.: 113 Supp. 28, pp.: 141–144, Jul. 1985.

Shishkina et al., Synthesis and properties of condensed heterocyclic derivatives of estra–4, 9–dien–17.beta.–ol–3–one (Abstract only), *Khim.–Farm. Zh.*, vol.: 8 (1), pp.: 7–11, 1974.

Sidky et al., Inhibition of Angiogenesis by Interferons: Effects on Tumor– and Lymphocyte–induced Vascular Responses, *Cancer Research*, vol.: 47, pp.: 5155–5161, Oct. 1, 1987.

Siracusa et al., The effect of microtubule– and microfilament–disrupting drugs on preimplantation mouse embryos (Abstract only), *Journal of Embryology and Experimental Morphology*, vol.: 60, pp.: 71–82, Dec. 1980.

Spyriounis et al., Copper (II) complex of an estradiol derivative with potent antiinflammatory properties (Abstract only), *Arch. Pharm.*, vol.: 324 (9), pp.: 533–536, 1991.

Srivastava, A. et al., The Prognostic Significance of Tumor Vascularity in Intermediate–Thickness (0.76–4.0 mm Thick) Skin Melanoma, *American Journal of Pathology*, vol.: 133 (2), pp.: 419–424, Nov. 1988.

Starkov et al., Mono– and Dialkylation of Guaiacol by Olefins on KU–2 Cation Exchanger (Abstract only), *Zhurnal Prikladnoi Khimji*, vol.: 41 (3), pp.: 688–690, 1968.

Taylor, S. et al., Protamine is an Inhibitor of Angiogenesis, *Nature*, vol.: 297, pp.: 307–312, May 27, 1982.

Vicente et al., In Vitro Activity of Thalidomide Against Mycobacterium avium Complex, *Archives of Internal Medicine*, vol.: 153 (4), pp.: 534, Feb. 22, 1993.

Wang et al., Photoaffinity labeling of human placental estradiol 17.beta.–dehydrogenase with 2– and 4–azidoestrone, 2– and 4–azidoestradiol (Abstract only), *Shengwu Huaxue Zazhi*, vol.: 8 (6), pp.: 715–718, 1992.

Weidner, N. et al., Tumor angiogenesis: A New Significant and Independent Prognostic Indicator in Early–Stage Breast Carcinoma, *Journal of the National Cancer Institute*, vol.: 84, pp.: 1875–1887, Dec. 16, 1992.

Weidner, N. et al., Tumor Angiogenesis Correlates with Metastasis in Invasive Prostate Carcinoma, *American Journal of Pathology*, vol.: 143 (2), pp.: 401–409, Aug. 1993.

Weidner, N. et al., Tumor Angiogenesis and Metastasis–Correlation in Invasive Breast Carcinoma, *New England Journal of Medicine*, vol.: 324 (1), pp.: 1–8, Jan. 3, 1991.

Welsch et al., Staphylostatic Activity of Some New Diphenols, Napthols, and Chalcones (Abstract only), *Experientia*, vol.: 11, pp.: 350–351, 1955.

White et al., Treatment of Pulmonary Hemangiomatosis with Recombinant Interferon Alfa–2a, *The New England Journal of Medicine*, vol.: 32 (18), pp.: 1197–1200, May 4, 1989.

Li, J., et al., (DN 103:65176) Catechol Formation of Fluoro– and Bromo–substituted Estradiols by Hamster Liver Microsomes. Evidence for Dehalogenation. (Abstract only), *CAPLUS: Molecular Pharmacology*, vol.: 27 (5), pp.: 559–565, 1985.

Nambara, T., et al., DN 82:43650: Analytical Chemical Studies on Steroids. LXXIII. Synthesis of Epimeric 2–Hydroxy–16–Chlorestrong Monomethyl Ethers (Abstract only), *HCAPLUS–Chemical and Pharmaceutical Bulletin*, vol.: 22 (10), pp.: 2455–2457, 1974.

Romanelli et al., Ethyl–p–Dimethylaminophenylacetate, *Organic Synthesis*, vol.: 5, pp.: 552, Oct. 24, 1973.

Yasuda et al., Accelerated differentiation in seminiferous tubules of fetal mice prenatally exposed to ethinyl estradiol (Abstract only), *Anat. Embryol. (Berl.)*, vol.: 174 (3), pp.: 289–299, 1986.

\* cited by examiner

ESTROGENIC COMPOUNDS AS ANTI-MITOTIC AGENTS

This application is a continuation of U.S. application Ser. No. 09/243,158 filed Feb. 2, 1999 now U.S. Pat. No. 6,528,676, which is a divisional of U.S. application Ser. No. 08/838,699 filed Apr. 25, 1997, now U.S. Pat. No. 5,892,069, which is a divisional of U.S. application Ser. No. 08/571,265 filed Dec. 12, 1995, now U.S. Pat. No. 5,661,143, which is a continuation of application Ser. No. 08/102,767, filed Aug. 6, 1993, now U.S. Pat. No. 5,504,074. This application is also a continuation of Ser. No. 09/780,650, filed Feb. 12, 2001, which is a continuation of Ser. No. 09/436,610, filed Nov. 9, 1999, abandoned, which is also a continuation of Ser. No. 09/243,158, filed Feb. 2, 1999 now U.S. Pat. No. 6,528,676. Each of the above-referenced applications is incorporated herein in its entirety.

BACKGROUND OF THE INVENTION

This invention relates to treating disease states characterized by abnormal cell mitosis.

Cell mitosis is a multi-step process that includes cell division and replication (Alberts, B. et al. In *The Cell*, pp. 652–661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from α and β tubulin polymerization and the hydrolysis of guanosine triphosphate (GTP). Microtubule formation is important for cell mitosis, cell locomotion, and the movement of highly specialized cell structures such as cilia and flagella.

Microtubules are extremely labile structures that are sensitive to a variety of chemically unrelated anti-mitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2-methoxyestradiol have been reported to inhibit cell division (Seegers, J. C. et al. *J. Steroid Biochem.* 32, 797–809 (1989); Lottering, M-L. et al. *Cancer Res.* 52, 5926–5923 (1992); Spicer, L. J. and Hammond, J. M. *Mol. and Cell. Endo.* 64, 119–126 (1989); Rao, P. N. and Engelberg, *J. Exp. Cell Res.* 48, 71–81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64, 119–126 (1989); Ravindra, R., *J. Indian Sci.* 64(c) (1983)), but not in others (Lottering, M-L. et al. *Cancer Res.* 52, 5926–5923 (1992); Ravindra, R., *J. Indian Sci.* 64 (c) (1983)). Estradiol metabolites such as 2-methoxyestradiol will inhibit cell division in selected in vitro settings depending on whether the cell culture additive phenol red is present and to what extent cells have been exposed to estrogen. (Seegers, J. C. et al. Joint NCI-IST Symposium. Biology and Therapy of Breast Cancer. Sep. 25–Sep. 27, 1989, Genoa, Italy, Abstract A58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtubule formation and tubulin polymerization and/or depolymerization. Compounds within the general formulae having said inhibiting activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

The bond indicated by C•••C is absent or, in combination with the C—C bond is the unit HC═CH.

Other features and advantages of the invention will be apparent from the following description of preferred embodiments thereof.

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below.

wherein:
I. $R_a$—$R_o$ are defined as follows:
A) each $R_a$, $R_b$, $R_c$, $R_d$, $R_e$, $R_f$, $R_i$, $R_j$, $R_k$, $R_L$, $R_m$, $R_o$, independently is —$R_1$, —$OR_1$, —$OCOR_1$, —$SR_1$, —F, —$NHR_2$, —Br, or —I; and $R_g$ is —$R_1$, —$OR_1$, —$OCOR_1$, —$SR_1$, —F, —$NHR_2$, —Br, —I, or —C≡CH;

or

B) each $R_a$, $R_b$, $R_c$, $R_f$, $R_k$, $R_L$, $R_o$, independently is $-R_1$, $-OR_1$, $-OCOR_1$, $-SR_1$, $-F$, $-NHR_2$, $-Br$, or $-I$; and each $R_d$, $R_e$, $R_i$, $R_j$, $R_m$, independently is $=O$, $-R_1$, $-OR_1$, $-OCOR_1$, $-SR_1$, $-F$, $-NHR_2$, $-Br$ or $-I$; and $R_g$ is $=O$, $-R_1$, $-OR_1$, $-OCOR_1$, $-SR_1$, $-F$, $-NHR_2$, $-Br$, $-I$, or $-C\equiv CH$;

and

II. Z' is defined as follows:

A) Z' is X, where X is $>COR_1$, $>\overset{O}{\underset{\|}{CC}}-R_1$, $>\overset{O}{\underset{\|}{CC}}-OR_1$, $>\overset{OH}{\underset{|}{CCH}}-R_1$, or $>\overset{OH}{\underset{|}{CCH}}-R_1$;

B) Z' is $=\overset{}{\underset{R_n}{C}}-X'-$ or $-X'-\overset{}{\underset{R_n}{C}}=$, where $R_n$ is $-R_1$, $-OR_1$, $-SR_1$, $-F$, $-NHR_2$, $-Br$ or $-I$;

and X' is X, as defined above; or X' is $>C=O$;

and

III. Z" is defined as follows:

A) Z is Y, where Y is $-O-$, $-\overset{R_1}{\underset{N}{|}}-$, $>CHR_1$, $>C=O$, $>\overset{R_1}{\underset{|}{C}}-(CH_2)_nOR_2$, $>\overset{R_1}{\underset{|}{C}}-(CH_2)_n-\overset{O}{\underset{\|}{C}}R_2$, $>\overset{R_1}{\underset{|}{C}}-(CH_2)_n-\overset{O}{\underset{\|}{C}}-OR_2$, $>\overset{R_1}{\underset{|}{C}}-(CH_2)_n-\overset{OH}{\underset{|}{C}}HR_2$, $>\overset{R_1}{\underset{|}{C}}-(CH_2)_n-\overset{OH}{\underset{|}{CH}}-OR_2$, $>\overset{R_1}{\underset{|}{C}}-NH(CH_2)_n-\overset{O}{\underset{\|}{C}}R_2$, $>\overset{R_1}{\underset{|}{C}}-NH(CH_2)_n-\overset{OH}{\underset{|}{CH}}R_2$, $>\overset{R_1}{\underset{|}{C}}-NH(CH_2)_n-\overset{OH}{\underset{|}{CH}}-OR_2$, $>\overset{R_1}{\underset{|}{C}}-NH(CH_2)_n-\overset{O}{\underset{\|}{C}}-OR_2$, $>\overset{R_1}{\underset{|}{C}}-NH(CH_2)_n-OR_2$, $>\overset{R_1}{\underset{|}{C}}-NH(CH_2)_n-R_2$, $>\overset{R_1}{\underset{|}{C}}-(CH_2)_n-\overset{O}{\underset{\|}{C}}NHCR_2$, $>\overset{R_1}{\underset{|}{C}}(CH_2)_n-NHCR_2$, $>\overset{R_1}{\underset{|}{C}}-(CH_2)_n-NH-\overset{OH}{\underset{|}{CH}}R_2$, $>\overset{R_1}{\underset{|}{C}}-(CH_2)_n-NH-CHOR_2$, or $>\overset{R_1}{\underset{|}{C}}-(CH_2)_n-NH-CH_2OR_2$, where n is 0–6;

B) Z" is $\overset{-Y-CH-}{\underset{R_n}{|}}$ or $\overset{-CH-Y-}{\underset{R_n}{|}}$, where $R_p$ is $-R_1$, $OR_1$, $-SR_1$, $-F$, $-NHR_2$, $-Br$ or $-I$ and Y is defined as in III(A);

and

IV. provided that when each $R_b$, $R_c$, $R_d$, $R_e$, $R_i$, $R_j$, $R_k$, $R_L$, $R_m$ and $R_o$ is H;

$R_f$ is $-CH_3$;
$R_g$ is $-OH$;
Z' is $>COH$; and
Z" is $>CH_2$;
then $R_a$ is not $-H$;

where, in each formula set forth above, each $R_1$ and $R_2$ independently is $-H$, or a substituted or unsubstituted alkyl, alkenyl or alkynyl group of up to 6 carbons. Those skilled in the art will appreciate that the invention extends to other compounds within the formulae given in the claims below, having the described characteristics. These characteristics can be determined for each test compound using the assays detailed below and elsewhere in the literature.

Figure 3:
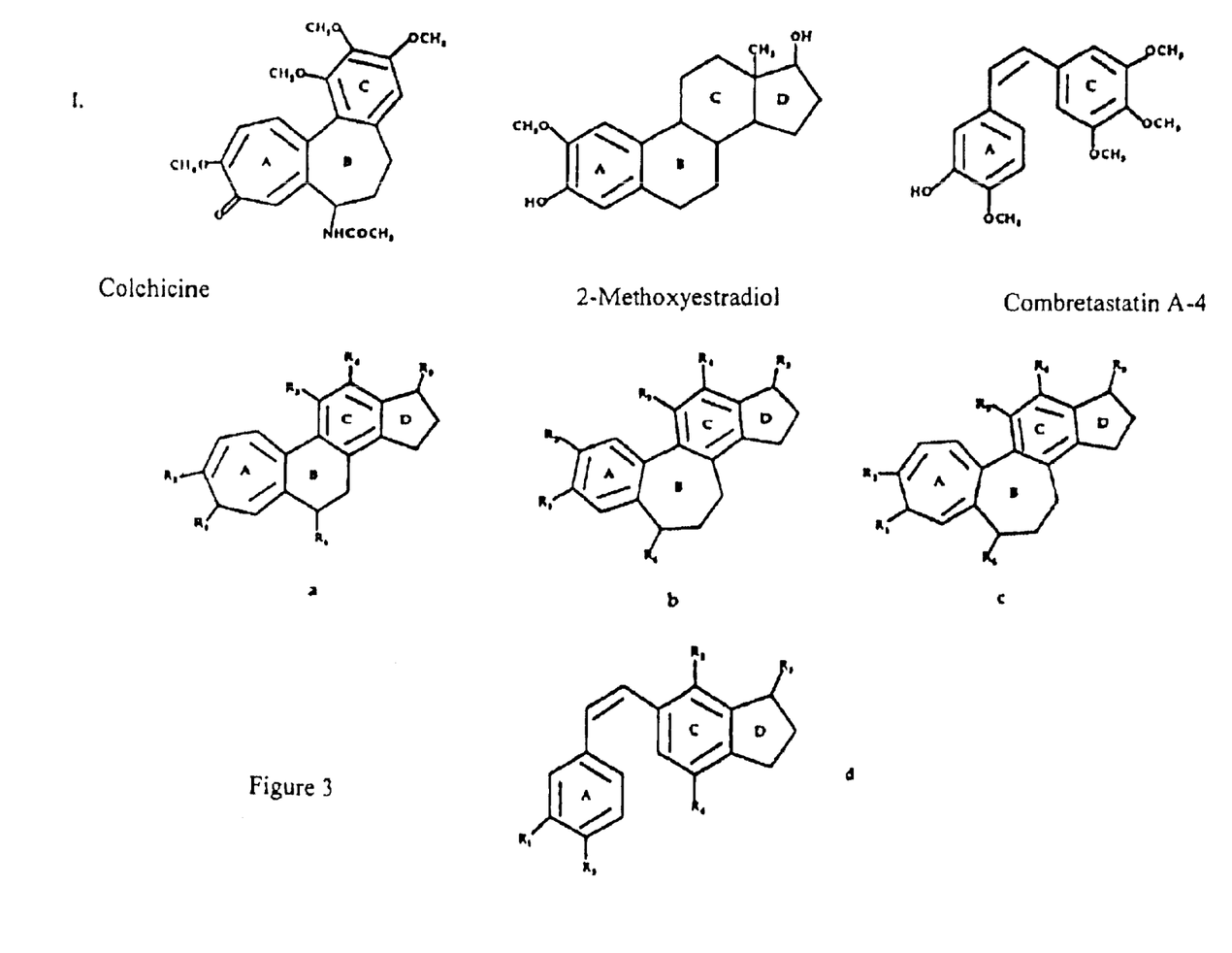
FIG. 3 depicts: I. colchicine, 2-methoxyestradiol and combretastatin A-4, and II. various estradiol derivatives comprising colchicine (a–c) or combretastatin A-4 (d) structural motifs as described below.

Without wishing to bind myself to specific mechanisms or theory, it appears that certain compounds that are known to inhibit microtubule formation, bind tubulin and exhibit anti-mitotic properties such as colchicines and combretastatin A-4 share certain structural similarities with estradiol. FIG. 3 illustrates the molecular formulae of estradiol, colchicines, combretastatin A-4, and improved estradiol derivatives that bind tubulin, inhibit microtubule assembly and exhibit anti-mitotic properties. Molecular formulae are drawn and oriented to emphasize structural similarities between the ring structures of colchicines, combretastatin A-4, estradiol, and certain estradiol derivatives. Estradiol derivatives are made by incorporating colchicines or combretastatin A-4 structural motifs into the steroidal backbone of estradiol.

FIG. 3, part I, depicts the chemical formulae of colchicine, 2-methoxyestradiol and combretastatin A-4. FIG. 3, part IIa–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \to R_6$ can independently be defined as $-R_1$, $-OR_1$, $-OCOR_1$, $-SR_1$, $-F$, $-NHR_2$, $-Br$, $-I$, or $-C\equiv CH$.

DETAILED DESCRIPTION OF THE INVENTION

Anti-Mitotic Activity In situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. Science 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity In vitro

Anti-mitotic activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 μl) contains 1.0M monosodium glutamate (ph 6.6), 1.0 mg/ml (10 μM) tubulin, 1.0 mM $MgCl_2$, 4% (v/v) dimethylsulfoxide and 20–75 μM of a composition to be tested. The 0.24 ml reaction mixtures are incubated for 15 min. at 37° C. and then chilled on ice. After addition of 10 μl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, D. A. *Helv. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index*, 11th Ed., Merck & Co., Inc., Rahway, N.J. USA (1989), pp. 583–584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents conventional in the art having regard to the type of formulation in question, for example, those suitable for oral administration may include flavoring agents.

EXAMPLE 1

Figure 1:
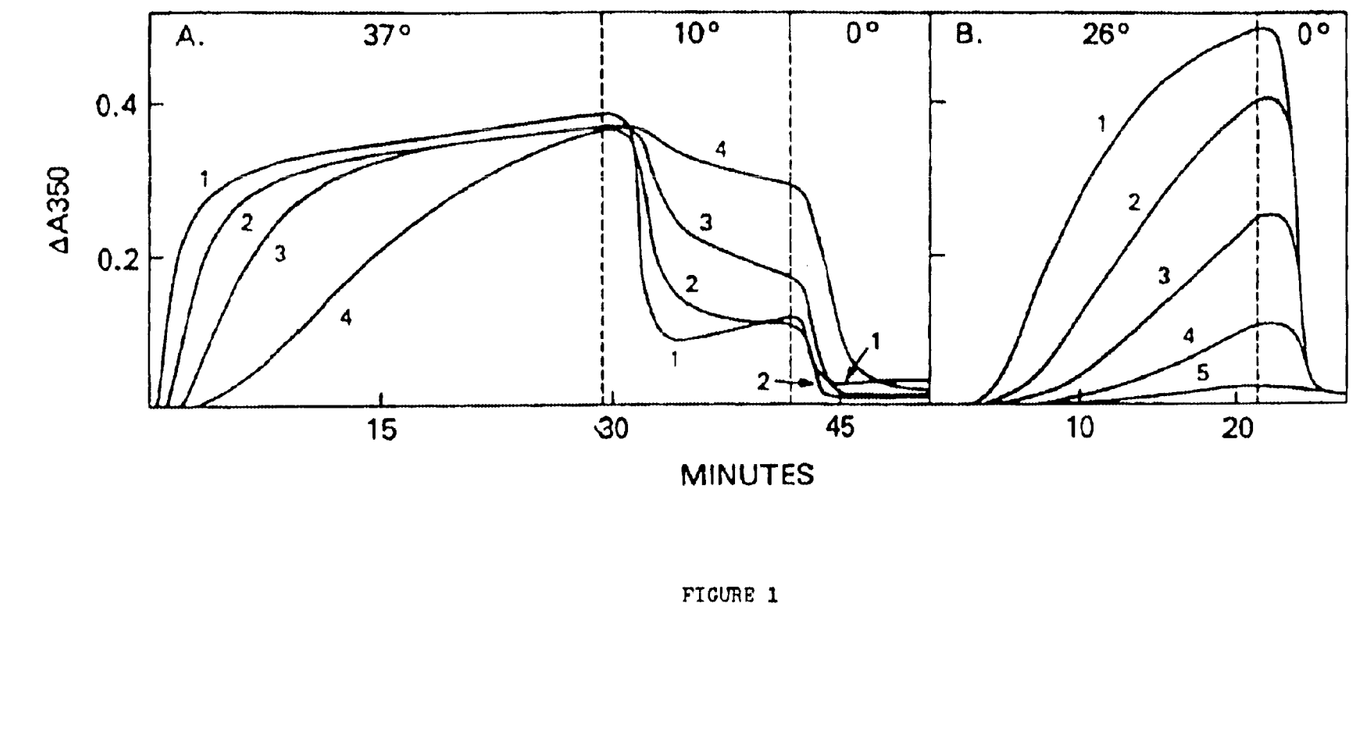
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 $\mu$M) tubulin, 1.0 mM MGCl$_2$, 4% (v/v) dimethylsulfoxide, and either 0 (curve 1), 20 $\mu$M (curve 2), 40 $\mu$M (curve 3), or 75 $\mu$M (curve 4) 2-methoxyestradiol. The 0.24 ml reaction mixtures were incubated for 15 min at 37° C. and chilled on ice. After addition of 10 $\mu$l of 2.5 mM GTP the reaction mixtures were transferred to cuvettes held at 0° C., and baselines were established. At time zero the temperature controller was set at 37° C. At the times indicated by the vertical dashed lines the temperature controller was set at the indicated temperatures.

B. Each reaction mixture contained 0.8 M monosodium glutamate (pH 6.6), 1.2 mg/ml (12 $\mu$M) tubulin, 4% (v/v) dimethylsulfoxide, and either 0 (curve 1), 1.0 $\mu$M (curve 2), 2.0 $\mu$M (curve 3), 3.0 $\mu$M (curve 4), or 4.0 $\mu$M (curve 5) 2-methoxyestradiol. The 0.24 ml reaction mixtures were incubated for 15 min at 26° C. and chilled on ice. After addition of 10 $\mu$l of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 $\mu$M 2-methoxyestradiol was added, and aliquots were placed on 200-mesh carbon coated copper grids and stained with 0.5% (w/v) uranyl acetate. TEM magnifications from 23,100× to 115,400× were used to visualize differences in tubulin morphology.

EXAMPLE 3

Figure 2:
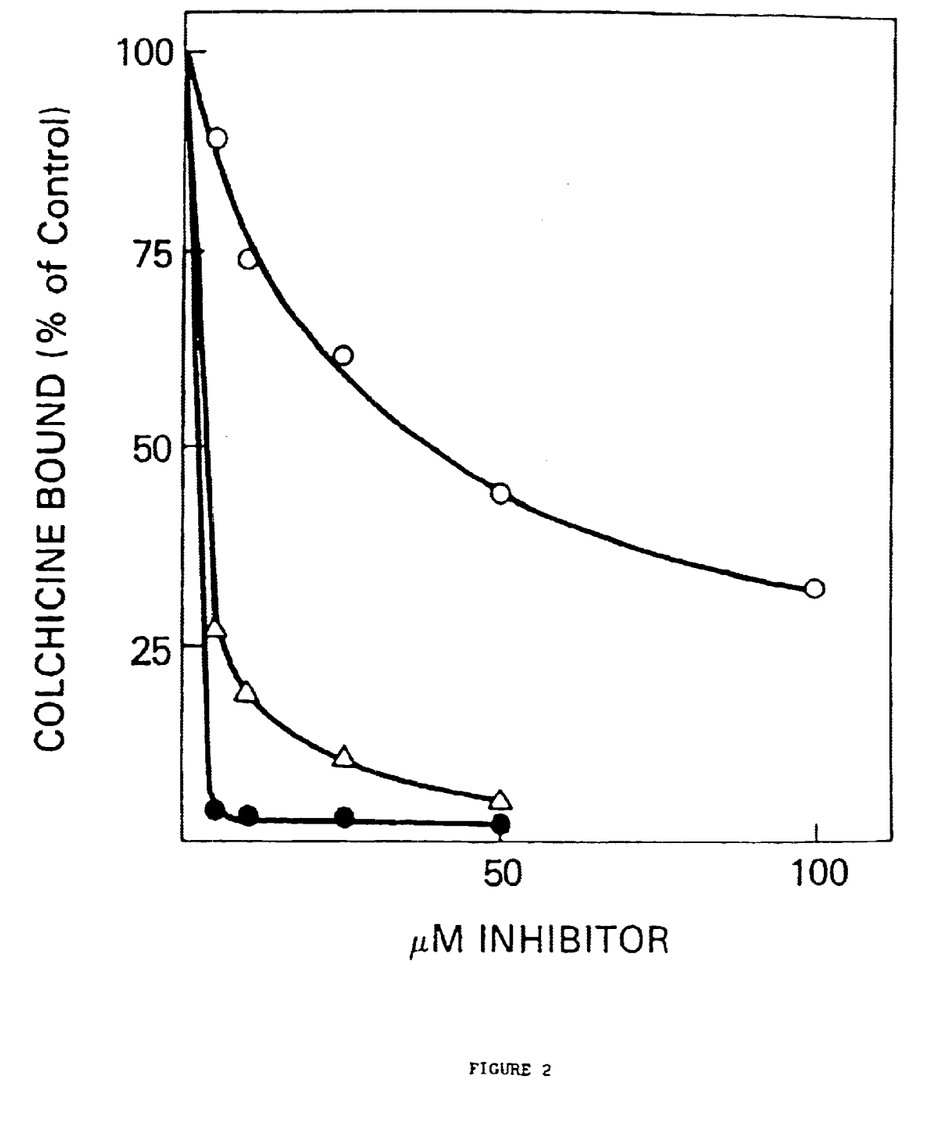
FIG. 2 is a graph illustrating the inhibition of colchicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 $\mu$M tubulin, 5% (v/v) dimethyl sulfoxide, 5 $\mu$M [$^3$H] colchicine, and inhibitor at the indicated concentrations. Incubation was for 10 min at 37° C. Symbols as follows: ○, 2-methoxyestradiol; ●, combretastatin A-4; Δ, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | IC$_{50}$ ($\mu$M ± S.D.) |
| --- | --- |
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |
| 2-Methoxyestradiol-3-O-methyl ether | >40 |
| 4-Methoxyestradiol | >40 |
| 4-Methoxyestradiol-3-O-methyl ether | >40 |

| Plant Products | IC$_{50}$ ($\mu$M ± S.D.) |
| --- | --- |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

IC$_{50}$ values are defined as the concentration of an estradiol derivative required to inhibit tubulin polymerization by 50%. IC$_{50}$ values were obtained in at least two independent experiments for non-inhibitory agents (IC$_{50}$>40 $\mu$M) and at least three independent experiments for inhibitory compounds. IC$_{50}$ values were obtained graphically, and average values are presented. S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.0 $\mu$M tubulin, 5% (v/v) dimethyl sulfoxide, 2 $\mu$M [$^3$H]colchicine, and 100 $\mu$M inhibitor. Incubation was for 10 min at 37° C. Average values obtained in three independent experiments are presented in the table, except for 2-methoxyestrone, which was only examined twice. S.D., standard deviation.

What is claimed is:

1. A method of treating ocular angiogenesis in a human or an animal, comprising administering to the human or animal an effective angiogenesis-inhibiting amount of a compound of the formula:

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that $R_a$ is not H.

2. The method of claim 1, wherein $R_a$ is —$OR_1$.
3. The method of claim 1, wherein $R_a$ is —$OCOR_1$.
4. The method of claim 1, wherein the compound is 2-methoxyestradiol.
5. The method of claim 2, wherein the compound is 2-methoxyestradiol.

* * * * *